(12) United States Patent
Park et al.

(10) Patent No.: US 6,936,240 B2
(45) Date of Patent: *Aug. 30, 2005

(54) METHOD FOR THE PREPARATION OF TECHNETIUM OR RHENIUM COMPLEX FOR RADIOPHARMACEUTICALS

(75) Inventors: Kyung Bae Park, Daejeon (KR); Sang Hyun Park, Seongnam-si (KR); Hui Jeong Gwon, Daejeon (KR); Sun Ju Choi, Daejeon (KR); Byung Chul Shin, Daejeon (KR); Young Don Hong, Daejeon (KR); Sang Mu Choi, Daejeon (KR); Woong Woo Park, Seoul (KR); Kwang Hee Han, Daejeon (KR); Beom Su Jang, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 239 days.

This patent is subject to a terminal disclaimer.

(21) Appl. No.: 10/287,133

(22) Filed: Oct. 31, 2002

(65) Prior Publication Data

US 2003/0228255 A1 Dec. 11, 2003

(30) Foreign Application Priority Data

Jun. 5, 2002 (KR) ................................ 10-2002-0031548

(51) Int. Cl.⁷ ........................ A61K 51/00; A61M 36/14
(52) U.S. Cl. ...................... 424/1.65; 424/1.11; 424/9.1; 534/14
(58) Field of Search ................................ 424/1.11, 1.37, 424/1.49, 1.65, 1.69, 1.73; 534/7, 10–14; 206/223, 569, 570

(56) References Cited

U.S. PATENT DOCUMENTS 6,344,178 B1 * 2/2002 Alberto et al. ............. 424/1.65

OTHER PUBLICATIONS

Neutral and Stereospecific Tc–99m Complexes by Zhi–Ping Zhuang et al., Nuclear Medicine & Biology, vol. 26, pp. 217–224, 1999.

Preparation of $^{99m}$Tc–N$_2$S$_2$ conjugates of chrysamine G. by Nancy A. Dezutter et al., Journal of Labelled Compounds and Radiopharm., 42, pp. 309–324 (1999).

Small and Neutral Tc$^V$O BAT, Bisaminoethanethiol (N$_2$S$_2$) Complexes, by Shunichi Oya et al., Nuclear Medicine & Biology, vol. 25, pp. 135–140, 1998.

* cited by examiner

*Primary Examiner*—Dameron L. Jones
(74) *Attorney, Agent, or Firm*—Bachman & LaPointe, P.C.

(57) ABSTRACT

The present invention relates to a method of preparing technetium or rhenium complex for radiopharmaceuticals, through reaction of pertechnetate or perrhenate with a ligand in the presence of a reducing agent, wherein the reducing agent is a borohydride exchange resin (BER). The borohydride exchange resin of the present invention has advantages of being stable in a wide range of Ph, including acidic or alkaline condition(Ph 2~14) and thus being applicable to biological materials as well as being easily removable through filtration when being administrated. Also since the radiolabelled complex is produced under conditions milder than those required for the conventional reducing agents as well as has high radiochemical purity and high labeling efficiency, the conventional reducing agents can be replaced by the BER of the present invention.

9 Claims, 19 Drawing Sheets

FIGURES

METHOD FOR THE PREPARATION OF TECHNETIUM OR RHENIUM COMPLEX FOR RADIOPHARMACEUTICALS

TECHNICAL FIELD

The present invention relates to a method of preparing technetium or rhenium complex for radiopharmaceuticals, through reaction of pertechnetate or perrhenate with a ligand in the presence of a reducing agent, wherein the reducing agent is a borohydride exchange resin (BER). Also, the present invention is concerned with a kit for radiolabelling with technetium or rhenium.

BACKGROUND ART

It is known that technetium(Tc)-99m ($^{99m}Tc$), as a radionuclide, has desirable nuclear properties, for example, a short half-life of 6 hours and 140 keV gamma ray emission energy suitable for obtaining gamma image, as well as a low price and a general utility, thus is commonly applied in nuclear medicine as radiopharmaceuticals for diagnosis and therapy. Tc-99m forms a stable complex with a compound having an unshared electron, such as isocyanate, amine, carboxy or thiol groups, and is thus used as an imaging agent or a radiolabelling agent for organs including lungs, liver and brain, or their tissues.

As isotopes of rhenium(Re), which is an analogous atom to Tc-99m, rhenium(Re)-186 ($^{186}Re$) and rhenium-188 ($^{188}Re$) are well known. The rhenium isotopes emit both beta ray suitable for therapy and gamma ray capable of imaging organs or living tissues. In practice, rhenium-186 and rhenium-188 are applied for alleviating pain in bone caused by secondary transition of various cancers, including prostate gland cancer, lung cancer and breast cancer, to bone. In addition, since Re-186 and Re-188 have similar chemical properties to technetium-99m, they can be applied for the radiolabelling methods using rhenium through improvement of the radiolabeling methods using Tc-99m (Lin, W. et al., *Eur. J. Nucl. Med.* 1997, 24, 590–595; Lewington, V. J. et al., *Eur. J. Nucl. Med.* 1993, 20, 66–74; Lewington, V. J. et al., *Phys. Med. Biol.* 1996, 41, 2027–2042; Hashimoto, K. et al., *Appl. Radiat. Isot.* 1996, 47, 195–199).

Using the metals technetium or rhenium, a target compound can be labeled through a process of forming a complex of a ligand with technetium or rhenium, and then performing a substitution reaction with another ligand. For example, when a lyophilized glucoheptonate is reacted with $^{99m}Tc$-sodium pertechnetate, $^{99m}Tc$-glucoheptonate complex is formed, and an active site of the complex is demonstrated to be $[Tc^v=O]^{3+}$ (Owunwanne, A. et al., *The Handbook of Radiopharmaceuticals*, Chapman & Hall Medical, London, UK, p. 94–95)

Based on this finding, production of technetium-labeled complex and its structure can be identified by performing a transchelation reaction with another ligand having an affinity higher than the bound ligand, glucoheptonate, and then by confirming a peak at a homologous position to $[Tc^v=O]^{3+}$ through thin layer chromatography (TLC) or reverse-phase high performance liquid chromatograph (HPLC).

Also, there was another attempt to form $^{99m}TcNCl_4^-$ precursor, where pertechnetate or perrhenate is refluxed with sodium azide ($NaN_3$) in the presence of strong HCl to form $^{99m}TcNCl_4^-$ complex, and $[^{99m}Tc^v{\equiv}N]^{2+}$ complex may be formed via a ligand-exchange reaction from the complex $^{99m}TcNCl_4^-$ (John Baldas and John Bonnyman Int. *J. Appl. Radiot. Isot.*, 1985, 36, 133–139; Florian Demaimay, Leontine Dazord, Alain Roucoux, Nicolas Noiret, Herri Patin and Annick Moisan, *Nuclear Medicine & Biology*, 1997, 24, 701–705).

In addition, Alberto, et al. disclose that $^{99m}Tc$-tricarbonyl complex of the low oxidation state(+1), a precursor which may be used in radiolabeling biomaterials, can be formed (Alberto R. et al., *J. Am. Chem. Soc.*, 1998, 120, 7987–7988; Egli A. et al., *J. Nucl. Med.*, 1999, 40(11), 1913–1917; Alberto R. et al., *Radiochimica Acta.*, 1997, 79, 99–103; Alberto R. et al., *J. Organometallic Chem.*, 1995, 493, 119–127; Reisgys M. et al., *Bioorganic & Medicinal Chemistry Letters*, 1997, 7(17), 2243–2246).

As described above, technetium or rhenium should be reduced prior to reaction of pertechnetate or perrhenate with a ligand to form complexes.

The reduction of Tc or Re may be achieved by electrolysis, or mostly in the presence of a reducing agent, including $SnCl_2.2H_2O$, ferrous ion, ferrous-ascorbate, formamidinesulphinic acid and sodium borohydride. The most commonly used reducing agent is tin chloride dihydrate ($SnCl_2.2H_2O$)

However, the reducing agent described above, tin chloride dihydrate ($SnCl_2.2H_2O$) is stable in an acidic condition, but it induces formation of precipitates in an alkaline condition. In contrast, sodium borohydride is stable at high pH, while being unstable at low pH. In addition, the reducing agents described above are typically utilized in a liquid state, when they are used excessively, impurities such as colloids can be generated, in addition to a danger of potentially residual toxicity, thereby limiting the amount of used reducing agents. These problems can be overcome through employment of a borohydride exchange resin to which borohydride ion ($BH_4^-$) is bound, with which the metal Tc or Re is reduced in a solid phase, and after that, borohydride ion can be removed by filtration, regardless of its used amount.

Because the reduction of Tc or Re has been achieved in stringent conditions as described above, there is a need for developing methods capable of reducing pertechnetate or perrhenate in a wide range of pH 2 to 14.

Leading to the present invention, the intensive and thorough research into a reducing agent for preparation of technetium or rhenium complex for radiopharmarceuticals, with the aim of solving the problems of the conventional reducing agents, resulted in the finding that technetium or rhenium complex with high radiochemical purity and excellent labeling efficiency is prepared by reacting pertechnetate or perrhenate with a ligand in the presence of borohydride exchange resin as a reducing agent.

DISCLOSURE OF THE INVENTION

It is therefore an object of the present invention to provide a method of preparing technetium or rhenium complex for radiopharmarceuticals.

It is another object of the present invention to provide a method of preparing technetium or rhenium complex through reduction of pertechnetate or perrhenate in the presence of borohydride exchange resin.

It is a further object of the present invention to provide a kit for radiorabelling with technetium or rhenium, comprising a ligand and a borohydride exchange resin.

BRIEF DESCRIPTION OF DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1A:
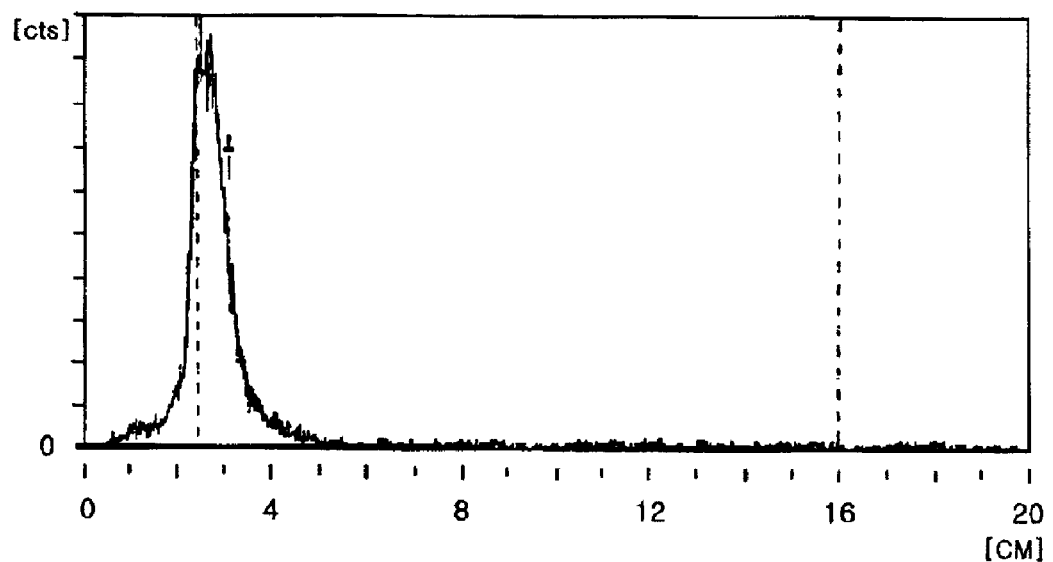
FIGS. 1a and 1b are results of thin-layer chromatography (TLC) of $^{99m}$Tc-glucoheptonate prepared in Step 1 of Example 1.

The present invention is directed to a method of preparing technetium or rhenium complex for radiopharmarceuticals.

In more detail, the preparation of technetium or rhenium complex is achieved by reacting pertechnetate (TcO$_4^-$) or perrhenate (ReO$_4^-$) with a ligand in the presence of a borohydride exchange resin (hereinafter referred to as "BER"), where the BER functions to reduce pertechnetate or perrhenate, thus being capable of directly combining technetium or rhenium to the ligand to form a complex.

Therefore, the BER of the present invention, as a novel reducing agent with ability to reduce pertechnetate and perrhenate, can be applied in all fields where the conventional reducing agents are used.

The BER carries borohydride ion (BH$_4^-$) bound to cation supported on the resin. The preferred cation is a quaternary ammonium functionality. The BER is preferably used in an amount sufficient for complete reduction of pertechnetate or perrhenate.

The borohydride ion (BH$_4^-$) can be immobilized on any of commercially available anion exchange resins containing quaternary ammonium group. Examples of the resins useful in the present invention include polystyrene, high-density polyethylene, and amberlite.

The BER has advantages of being stable in a wide range of pH, including strong acidic and strong alkaline conditions, and thus being applicable to biomolecules, in addition the borohydride ion of the BER is easily removable by filtration when the biomolecules are applied to the BER.

The ligand useful in the present invention is any one selected from those capable of forming complex with technetium or rhenium, preferably, monodentate, and more preferably, bidentate or tetradentate, which serve to stereochemically stabilize the metal when complex is formed.

The ligand has a functional group including amine, carboxy group, thiolate, nitrido, isocyanate, alcohol, ester, halogen atom, alkoxy group, sulfonic acid, nitro group, amide group, nitrile group, and isonitrile group. In detail, the ligand is preferably selected from the group consisting of nitrido, glucoheptonate, L-cysteine, L-cysteine.HCl.H$_2$O, diamine disulfide, dimercaptosuccinic acid, thio-β-D-glucose, methylene diphosphate, diethylenetriamine pentaacetic acid, and N-[2-((2-triphenyl methyl)thio)ethyl] acethyl]-S-(triphenyl methyl)-2-aminoethanethiol.

In addition, according to the present invention, because the BER is stable in a wide range of pH including extreme acidic and alkaline pH, it is directly applied to the biomolecules, thus they can be used as ligands. The preferred biomolecules are human serum albumin, peptide, and human immunoglobulin.

In accordance with the present invention, technetium (that is, Tc-99m or $^{99m}$Tc) or rhenium (that is, Re-188 or $^{188}$Re), supplied in a form of pertechnetate or perrhenate, respectively, is reduced in the presence of the BER, thus being converted to a lower oxidation state capable of forming complex. The reduced technetium or rhenium is then reacted with a ligand to form a complex, where the reaction is performed in situ under inert gas atmosphere, for example, nitrogen atmosphere.

The method of the present invention does not have a limitation in an order of adding the ligand and pertechnetate or perrhenate.

The ligand and pertechnetate or perrhenate may be added together to the borohydride exchange resin, or according to a predetermined order. Also, pertechnetate or perrhenate can be added to a mixture of a lyophilized ligand and the BER.

The reduction of pertechnetate or perrhenate is achieved at room temperature in a proper medium depending on the used chemical reagents. Then, the reactant, which may contain a radiolabelled complex of interest, is filtered with a 0.2 μm membrane filter, yielding a product with high radiochemical purity and high labeling efficiency. In case of being suitable for use as radiopharmaceuticals, immediately after the filter-purification step, the complexes may be applied for medical imaging. When technetium is employed, technetium is typically reduced using only the BER, in which the reaction is completed in about 10 to about 30 minutes at room temperature, depending on the used chemical reagents and conditions. In contrast, since rhenium has electron density higher than technetium and thus forms stronger bonds, its reduction is preferably carried out in combination with other reducing agents used in the art, and completed in about 10 to about 30 minutes at 80 to 100° C. In accordance with embodiments of the present invention, technetium or rhenium-labeled complexes, prepared according to the method of the present invention, have a radiochemical purity of 99% and a labeling efficiency of over 95% (see, FIGS. 1a to 13).

Additionally, the present invention is directed to a kit for radiolabelling with technetium or rhenium, comprising a ligand and a borohydride exchange resin. Before the kit is applied to patients, pertechnetate or perrhenate should be added thereto to form radiolabelled complex. The kit is preferably lyophilized or dried at room temperature to guarantee its stability during storage. When being impossible to be lyophilized, the kit can be stored in a frozen state. The ligand and borohydride exchange resin are preferably stored in a tightly sealed sterile vessel which contains no exoergic materials, and a reaction vessel is preferably filled with inert gas, such as nitrogen. To make sure of its stability during storage, the kit can additionally contain an additive commonly used in the art (for example, sodium citrate and manitol), use of which is well known in the art.

In accordance with the present invention, using the method of preparing technetium or rhenium radiopharmarceuticals and the kit for providing the radiopharmarceuticals, with which a complex of a ligand and Tc-99m or Re-188 is formed after reduction of pertechnetate or perrhenate metal by the borohydride exchange resin, the radiolabelled complex is produced under conditions milder than those required for the conventional reducing agents, as well as having high radiochemical purity and high labeling efficiency. Especially, when technetium is used, radiolabelled complexes with high radiochemical purity and high labeling efficiency are prepared using only the BER as a reducing agent. Thus, the conventional reducing agents can be replaced by the BER of the present invention.

In embodiments of the present invention, all of radiolabelled compounds prepared using the BER or tin chloride dihydrate ($SnCl_2.2H_2O$) as a reducing agent are distributed in bone. Those are variably distributed in vivo, depending on reducing agent. In addition, radiolabelled complexes formed using tin chloride dihydrate are predominantly distributed in brain, while those formed using the BER are dominantly distributed in liver, thus allowing selection of a reducing agent depending on organs or tissues to which they will be applied when preparing radiopharmaceuticals.

The present invention will be explained in more detail with reference to the following examples in conjunction with the accompanying drawings. However, the following examples are provided only to illustrate the present invention, and the present invention is not limited to them.

EXAMPLE 1

Preparation of $^{99m}$Tc-L-cysteine

STEP 1: Preparation of $^{99m}$Tc-glucoheptonate

Lyophilized glucoheptonate was first added to a vial containing 0.5 ml of a liquid solution of $Na^{99m}TcO_4$ (25 mCi) The reaction mixture was well mixed for about 20 sec at room temperature under nitrogen atmosphere, and the reaction was carried out until that the glucoheptonate powder was completely dissolved, thus forming $^{99m}$Tc-glucoheptonate.

STEP 2: Preparation of $^{99m}$Tc-L-cysteine

A liquid solution of L-cysteine-$HCl.H_2O$, prepared by dissolving 1.0 mg of L-cysteine.$HCl.H_2O$ in 0.1 ml distilled water, and 0.1 ml of $^{99m}$Tc-glucoheptonate (5 mCi) prepared in the Step 1 were added simultaneously to a vacuum vial containing 5.0 mg BER, and transchelation reaction was then performed. The reaction mixture was well mixed for 30 minutes at room temperature under nitrogen atmosphere. After mixing, the reaction mixture was filtered using a 0.2 μm membrane filter, thus giving $^{99m}$Tc-L-cysteine, as a technetium-labeled compound of interest.

EXAMPLE 2

Preparation of $^{99m}$Tc-DADS

To a vacuum vial containing 5.0 mg of BER were simultaneously added $^{99m}$Tc-glucoheptonate prepared in Step 1 of Example 1, and a liquid solution of 3,3,10,10-tetramethyl-1,2-dithia-5,8-diazacyclodecane (diamine disulfide; DADS) as a ligand, prepared by dissolving 0.1 mg thereof in 0.1 ml distilled water, and transchelation was performed according to the same method as in Example 1, resulting in formation of $^{99m}$Tc-diamine disulfide ($^{99m}$Tc-DADS), as a technetium-labelled compound of interest.

EXAMPLE 3

Preparation of $^{99m}$Tc$(H_2O)_3(CO)_3$L-cysteine

STEP 1: Preparation of a precursor [$^{99m}$Tc$(H_2O)_3(CO)_3$]$^+$ 8 mg of sodium bicarbonate and 15 mg of BER were put into a 10 ml vial, and the vial was sealed with a rubber cover and held at room temperature for 30 minutes under CO gas. The vial was then supplemented with 6 ml of Tc-99m sodium pertechnetate ($Na^{99m}TcO_4$) (60 mCi) dissolved in physiological saline, and the reaction mixture was heated at 75° C. for 30 minutes under CO gas. After being cooled to room temperature in a chamber containing ice, and neutralized with 0.6 ml phosphate buffer (1M, pH 7.4), the reaction mixture was then filtered with a 0.22 μm membrane filter, giving a $^{99m}$Tc-tricarbonyl precursor [$^{99m}$Tc $(H_2O)_3(CO)_3$]$^+$.

STEP 2: Preparation of $^{99m}$Tc$(H_2O)_3(CO)_3$ L-cysteine 0.1 ml of 10 mM L-cysteine.$HCl.H_2O$ was mixed with 0.9 ml of the $^{99m}$Tc-tricarbonyl precursor [$^{99m}$Tc $(H_2O)_3(CO)_3$]$^+$, prepared in the above Step 1, and the mixture was heated at 75° C. for 30 minutes. After being cooled to room temperature in a chamber containing ice, the reaction mixture was filtered with a 0.22 μm membrane filter, giving $^{99m}$Tc$(H_2O)_3(CO)_3$ L-cysteine as a technetium-labeled compound of interest.

EXAMPLE 4

Preparation of $^{99m}$Tc-DMSA

To a vacuum vial containing 5.0 mg of BER were simultaneously added a liquid solution of dimercaptosuccinic acid (DMSA) prepared by dissolving 1.0 mg thereof in 0.1 ml distilled water, and 0.1 ml of a liquid solution of Tc-99m sodium pertechnetate (5 mCi). The reaction mixture was stirred for 30 minutes at room temperature. Thereafter, the reaction mixture was filtered with a 0.2 μm membrane filter, giving $^{99m}$Tc-L-dimercaptosuccinic acid ($^{99m}$Tc-DMSA), as a technetium-labeled compound of interest.

EXAMPLE 5

Preparation of $^{99m}$Tc-methylene Diphosphate

The same procedure as in Example 4 was carried out, except that a liquid solution of methylene diphosphate (MDP) prepared by dissolving 1.0 mg thereof in 0.1 ml distilled water, and 0.1 ml of a liquid solution of Tc-99m sodium pertechnetate (5 mCi) were simultaneously added to a vacuum vial containing 5.0 mg of BER, resulting in the formation of $^{99m}$Tc-methylene diphosphate ($^{99m}$Tc-MDP) as a technetium-labeled compound of interest.

EXAMPLE 6

Preparation of $^{99m}$Tc-MAMA

To a vacuum vial containing 5.0 mg of BER were simultaneously added a liquid solution of N-[2-((2 ((triphenyl methyl)thio)ethyl)acetyl)-S-(triphenyl methyl)-2-aminoethanethiol (monoamine monoamide-Tr2 or MAMA-Tr2) prepared by dissolving 1.0 mg thereof in 0.1 ml distilled water, and 0.1 ml of a liquid solution of Tc-99m sodium pertechnetate (5 mCi). After being well mixed, the reaction mixture was stirred at 100° C. for 15 min, and then filtered with a 0.2 μm membrane filter, resulting in the formation of $^{99m}$Tc-L-N-[2-((2-((triphenyl methyl)thio)ethyl)acetyl)-S-(triphenyl methyl)-2-aminoethanethiol ($^{99m}$Tc-monoamine monoamide or $^{99m}$Tc-MAMA) as a technetium-labeled compound of interest.

EXAMPLE 7

Preparation of $^{99m}$Tc-human Serum Albumin

The same procedure as in Example 4 was carried out, except that a liquid solution of human serum albumin (HSA) prepared by dissolving 1.0 mg thereof in 0.1 ml distilled water and then adjusting to pH 2.5 using 0.5 N HCl, and 0.1 ml of a liquid solution of Tc-99m sodium pertechnetate (5 mCi) were simultaneously added to a vacuum vial containing 5.0 mg of BER, resulting in the formation of $^{99m}$Tc-human serum albumin ($^{99m}$Tc-HSA) as a technetium-labeled compound of interest.

EXAMPLE 8

Preparation of $^{99m}$TcN-DADS

STEP 1: Preparation of $^{99m}$Tc-Nitrido

The same procedure as in Example 4 was carried out, except that a liquid solution of sodium azide (NaN$_3$) prepared by dissolving 1.0 mg thereof in 0.1 ml distilled water, and 0.1 ml of a liquid solution of Tc-99m sodium pertechnetate (5 mCi) were simultaneously added to a vacuum vial containing 5.0 mg of BER, resulting in the formation of $^{99m}$TcNCl$_4^-$. $^{99m}$Tc-Nitrido was formed by substituting ligand of $^{99m}$TcNCl$_4^-$.

STEP 2: Preparation of $^{99m}$TcN-DADS

The same procedure as in Example 4 was carried out, except that $^{99m}$Tc-Nitrido prepared in Step 1 of Example 8 and a liquid solution of 3,3,10,10-tetramethyl-1,2-dithia-5,8-diazacyclodecane (diamine disulfide or DADS) as a ligand prepared by dissolving 1.0 mg thereof in 0.1 ml distilled water were simultaneously added to a vacuum vial containing 5.0 mg of BER, resulting in the formation of $^{99m}$Tc-diamine disulfide ($^{99m}$Tc-DADS) as a technetium-labelled compound of interest.

EXAMPLE 9

Preparation of $^{99m}$Tc-1-thio-β-D-glucose

The same procedure as in Example 4 was carried out, except that a liquid solution of 1-thio-β-D-glucose prepared by dissolving 2.0 mg thereof in 0.1 ml distilled water and then adjusting to pH 4.0 with a solution of 0.005 N HCl, and 0.1 ml of a liquid solution of Tc-99m sodium pertechnetate (5 mCi) were simultaneously added to a vacuum vial containing 5.0 mg of BER, resulting in the formation of $^{99m}$Tc-1-thio-β-D-glucose as a technetium-labeled compound of interest.

EXAMPLE 10

Preparation of $^{99m}$Tc-glycylglycylglycine

In order to investigate the ability of Tc-99m to label peptide and protein, a liquid solution of glycylglycylglycine prepared by dissolving 1.0 mg thereof in 0.1 ml distilled water, and 0.1 ml of a liquid solution of Tc-99m sodium pertechnetate (5 mCi), were simultaneously added to a vacuum vial containing 5.0 mg of BER, followed by performing the same procedure as in Example 4, thus forming $^{99m}$Tc-glycylglycylglycine as a technetium-labeled compound of interest.

EXAMPLE 11

Preparation of $^{99m}$Tc-human Immunoglobulin G

The same procedure as in Example 4 was carried out, except that a liquid solution of human immunoglobulin G (IgG) prepared by dissolving 1.0 mg thereof in 0.1 ml distilled water, and 0.1 ml of a liquid solution of Tc-99m sodium pertechnetate (5 mCi) were simultaneously added to a vacuum vial containing 5.0 mg of BER, thus forming $^{99m}$Tc-IgG as a technetium-labeled compound of interest.

EXAMPLE 12

Preparation of $^{188}$Re-DADS

A liquid solution of 3,3,10,10-tetramethyl-1,2-dithia-5,8-diazacyclodecane (diamine disulfide, DADS) prepared by dissolving 1.0 mg thereof in 0.1 ml distilled water, a solution of 0.5 mg SnCl$_2$.2H$_2$O dissolved in 0.1 ml of 0.005 N HCl, and 0.1 ml of a liquid solution of Re-188 sodium perrhenate (3 mCi) were simultaneously added to a vial containing 5.0 mg of BER under a nitrogen atmosphere. After being well mixed, the reaction mixture was stirred for 15 min at 85° C., and filtered with a 0.2 μm membrane filter, giving $^{188}$Re-diamine disulfide ($^{188}$Re-DADS), as a rhenium-labeled compound of interest.

EXAMPLE 13

Preparation of $^{188}$Re-Nitrido

A liquid solution of sodium azide (NaN$_3$) prepared by dissolving 1.0 mg thereof in 0.1 ml distilled water, a solution of 0.5 mg SnCl$_2$.2H$_2$O dissolved in 0.1 ml of 0.005 N HCl, and 0.1 ml of a liquid solution of Re-188 sodium perrhenate (3 mCi) were simultaneously added to a vial containing 5.0 mg of BER under nitrogen atmosphere. After being well mixed, the reaction mixture was stirred for 15 min at 100° C., and filtered with a 0.2 μm membrane filter to give $^{188}$Re-NCl$_4^-$.$^{188}$Re-Nitrido was then formed under an acidic condition using HCl.

Radiochemical purities and labeling efficiencies of radiolabelled compounds with Tc-99m or Re-188 as prepared above were evaluated, as follows.

EXPERIMENTAL EXAMPLE 1

Assay for Radiochemical Purity and Labeling Efficiency of $^{99m}$Tc-L-cysteine

The assay for formation and structure of radiolabelled compounds with $^{99m}$Tc pertechnate ion, $^{99m}$TcO$_2$ and technetium can be ahcieved by investigating their position using an instant thin-layer chromatography (ITLC) system and HPLC. In this experimental example, radiochemical purity and labeling efficiency of $^{99m}$Tc-glucoheptonate prepared in the Step 1 of Example 1, of which structure is known, were determined by performing chromatography using the system ITLC and reverse phase HPLC, and used as a standard labeling compound.

Figure 1B:
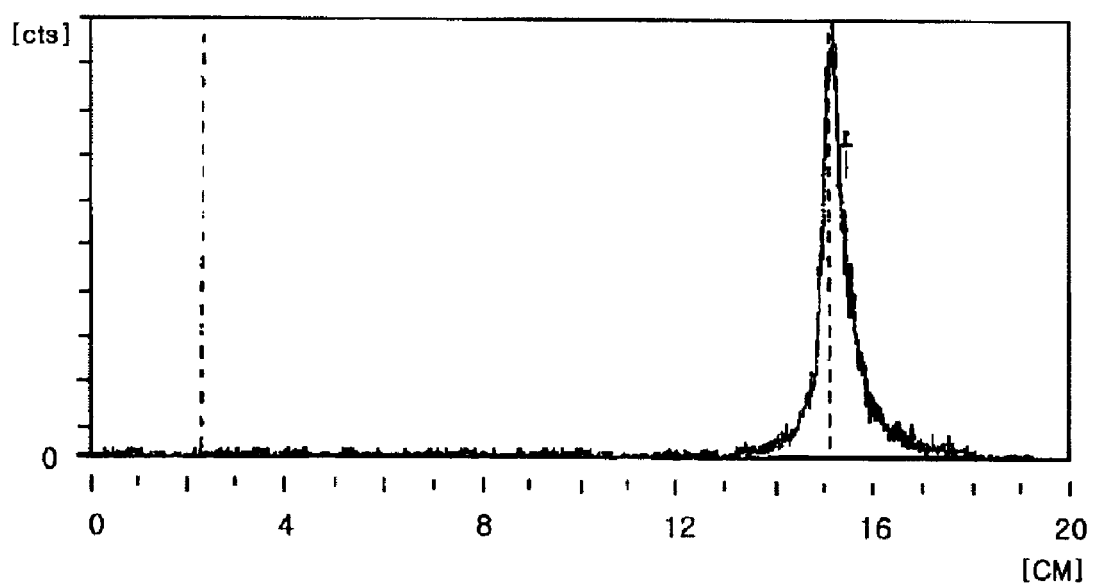

FIGS. 1a and 1b show the results of thin-layer chromatography for $^{99m}$Tc-glucoheptonate, by performing ITLC on silica gel impregnated glass fiber sheets, using acetone and physiological saline as a development solvent, respectively.

Figure 1C:
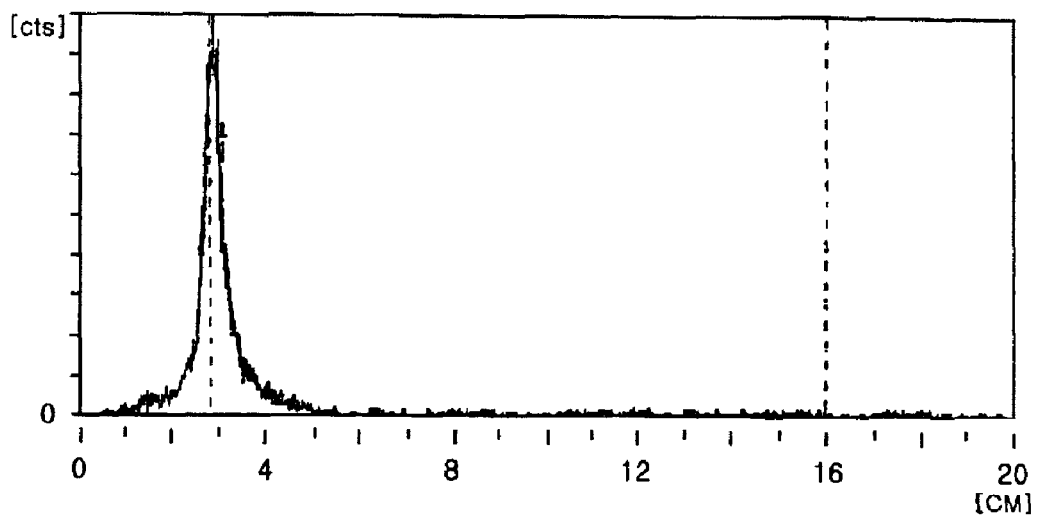
FIGS. 1c and 1d are results of TLC of $^{99m}$Tc-cysteine prepared in Example 1.
Figure 1D:
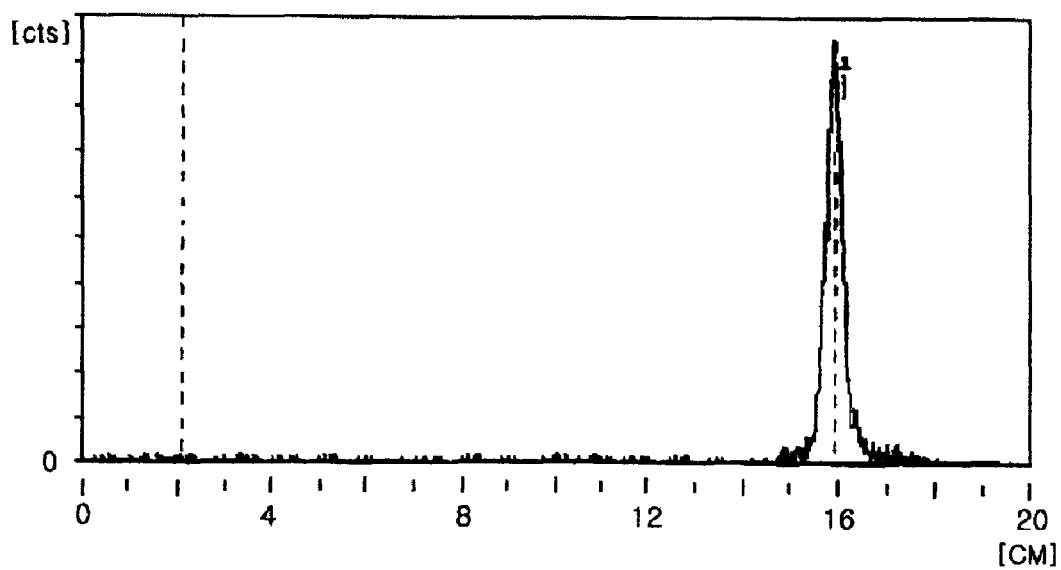

In case of $^{99m}$Tc-L-Cysteine, prepared by transchelation in Example 1, ITLC-SG (silica gel) was performed using the same development solvent as in $^{99m}$Tc-glucoheptonate, based on the result of ITLC of $^{99m}$Tc-glucoheptonate, and the results are given FIGS. 1c and 1d, in which acetone and physiological saline, respectively, were used as a development solvent.

As apparent in FIG. 1c, showing a result of ITLC-SG of $^{99m}$Tc-L-Cysteine using acetone as a development solvent, there was no observation of a peak of $^{99m}$TcO$_4^-$ at the solvent front, which is expected to migrate with the solvent front. As shown in FIG. 1d, $^{99m}$TcO$_2$ was not observed at the origin. These results indicate that $^{99m}$Tc-L-Cysteine complexes having excellent labeling efficiency were formed.

Radiochemical purity of the complex $^{99m}$Tc-L-cysteine, prepared in Example 1, was measured using HPLC involving a C-18 reverse-phase column as a stationary phase and a phosphate-buffered triethylammonium solution/methanol solvent mixture as a mobile phase, while maintaining a flow rate of 1 ml/min. The result is given FIG. 1e.

Figure 1E:
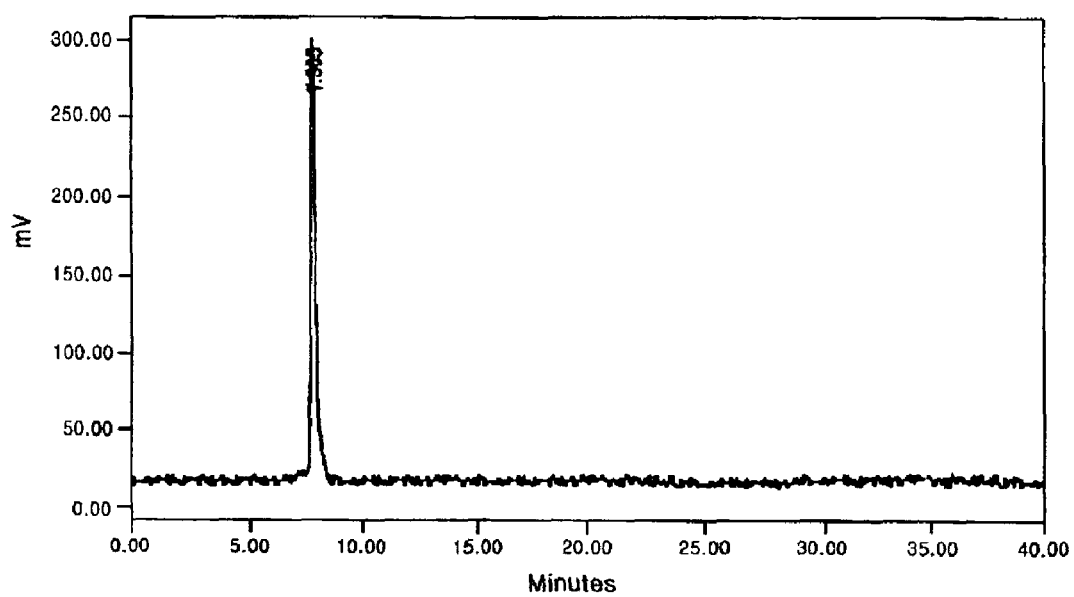
FIG. 1e is a result of high performance liquid chromatography (HPLC) of $^{99m}$Tc-cysteine prepared in Example 1.

As shown in FIG. 1e, two peaks were seen, in which one at retention time of 10 min is equivalent to a peak of $^{99m}$TcO$_4^-$, and the other at retention time of 7.9 min is a peak of the compound of interest, indicating formation of $^{99m}$Tc-L-cysteine complex with labeling efficiency of over 98%.

EXPERIMENTAL EXAMPLE 2

Assay for Radiochemical Purity and Labeling Efficiency of $^{99m}$Tc-diamine Disulfide Radiochemical purity and labeling efficiency of $^{99m}$Tc-diamine disulfide ($^{99m}$Tc-DADS) were evaluated according to the same method as in Example 1 using ITLC-SG and reverse-phase HPLC.

Figure 2A:
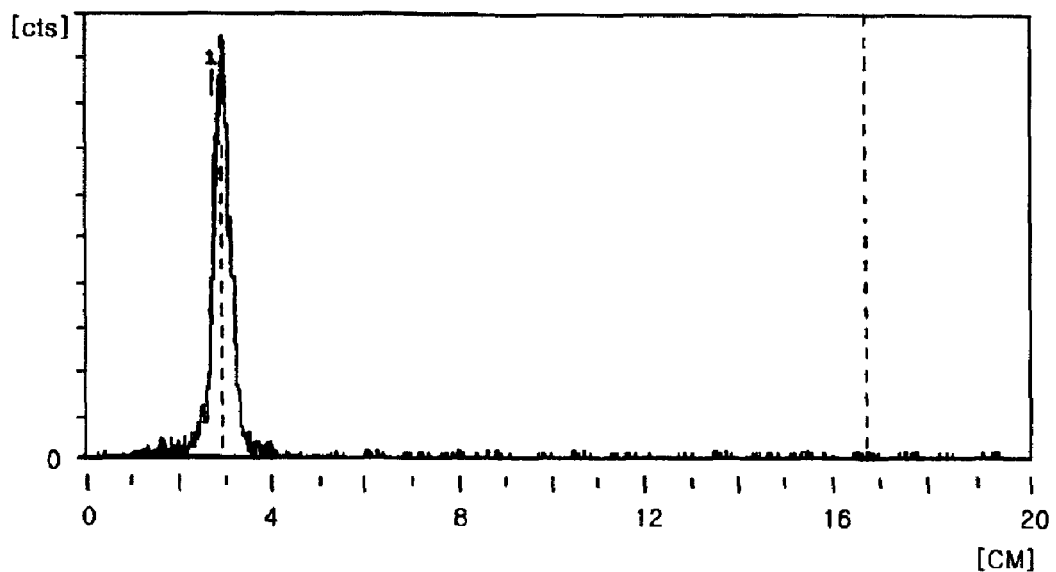
FIGS. 2a and 2b are results of TLC of $^{99m}$Tc-diamine disulfide prepared in Example 2.
Figure 2B:
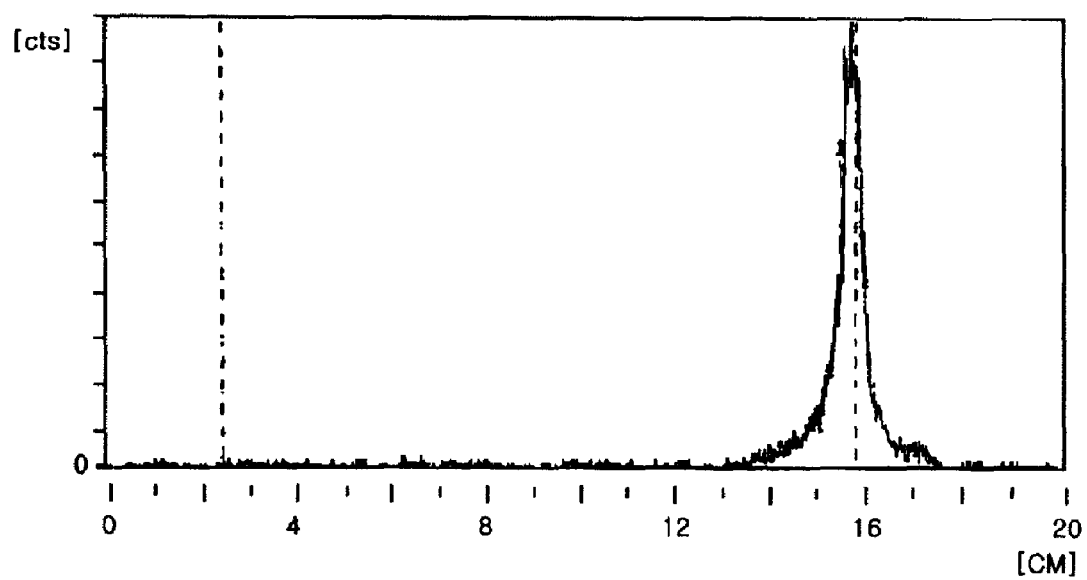

ITLC-SG was performed using acetone or a methanol/HCl (99.5:0.5) solvent mixture as a developer, and the results are given FIGS. 2a and 2b, respectively. In addition, reversed-phase HPLC was carried out using a C-18 reverse-phase column as a stationary phase and a phosphate-buffered triethylammonium solution/methanol solvent mixture as a mobile phase, while maintaining a flow rate of 1 ml/min, and the result is given in FIG. 2c.

Figure 2C:
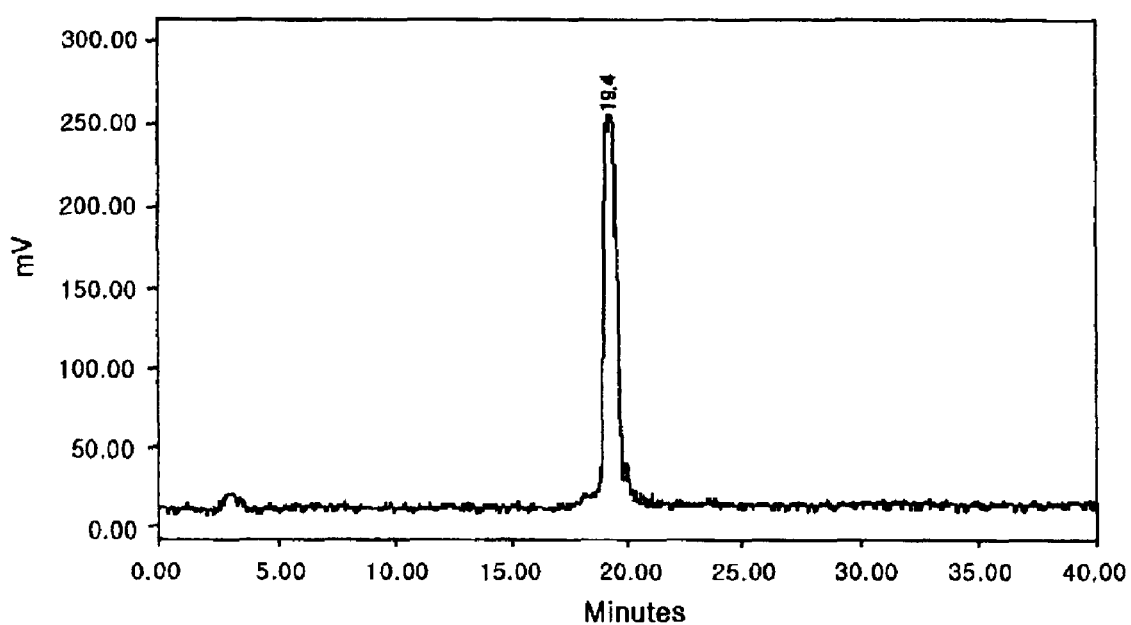
FIG. 2c is a result of HPLC of $^{99m}$Tc-diamine disulfide prepared in Example 2.

As shown in FIG. 2c, there was observed only one peak with a retention time of 19.4 min, which is a retention time of the compound of interest, demonstrating the formation of $^{99m}$Tc-DADS having labeling efficiency of over 99%.

EXPERIMENTAL EXAMPLE 3

Figure 3A:
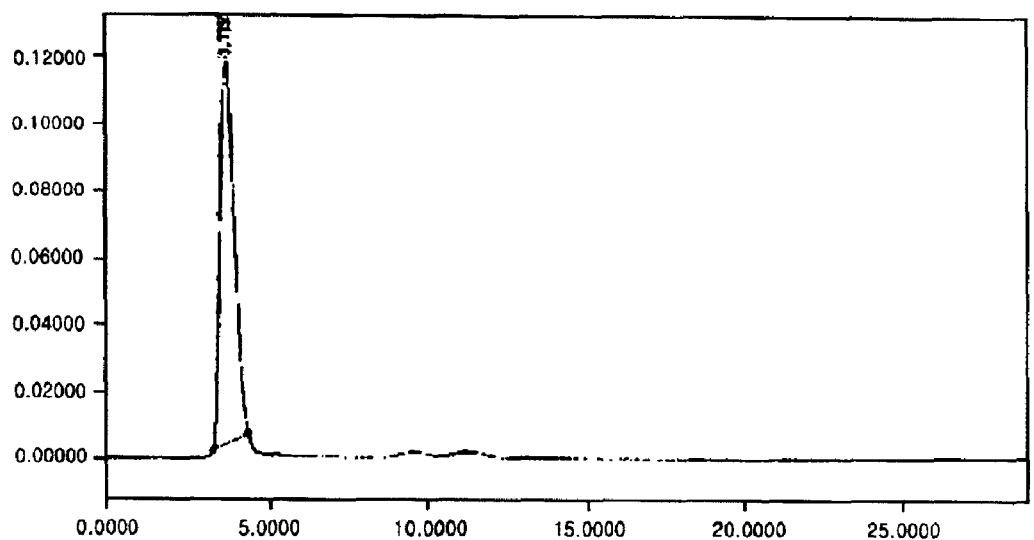
FIG. 3a is a result of HPLC of $^{99m}$Tc-tricarbonyl precursor prepared in Example 3.
Figure 3B:
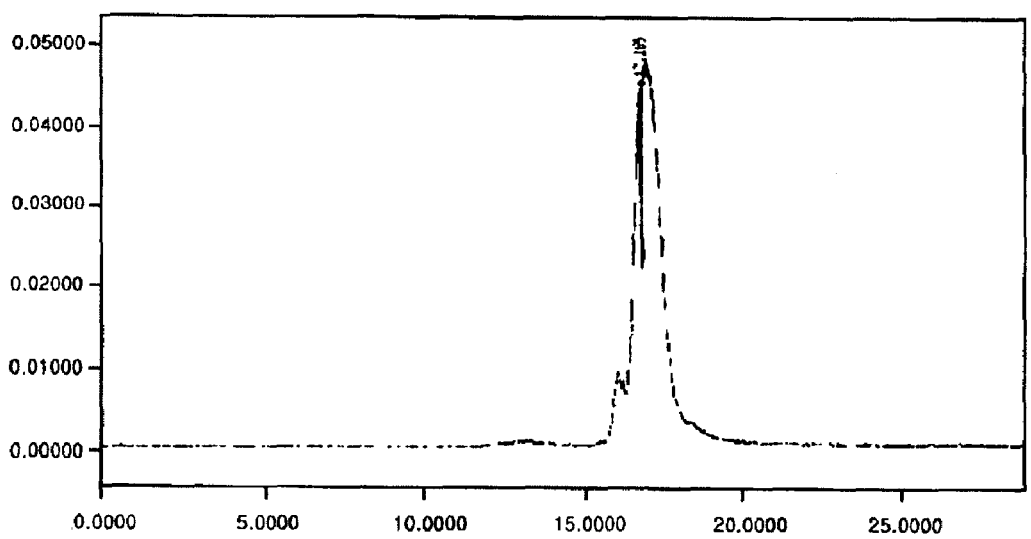
FIG. 3b is a result of HPLC of $^{99m}$Tc-(H$_2$O)$_3$ (CO)$_3$L-cysteine prepared in Example 3.

Assay for Radiochemical Purity and Labeling Efficiency of $^{99m}$Tc-(H$_2$O)$_3$ (CO)$_3$ L-cysteine Radiochemical purities and labeling efficiencies of the $^{99m}$Tc-tricarbonyl precursor [$^{99m}$Tc(H$_2$O)$^3$ (CO)$_3$]$^+$ and $^{99m}$Tc (H$_2$O)$_3$ (CO)$_3$ L-cysteine, prepared in Example 3, were evaluated by performing HPLC on a C-18 reverse-phase column as a stationary phase, employing a concentration gradient consisting of a phosphate-buffered triethylammonium solution/methanol solvent (pH 2.25) as a mobile phase, while maintaining a flow rate of 1 ml/min, and the results are given in FIGS. 3a and 3b, respectively.

As shown in FIG. 3a, one peak having a retention time of 4 min was found, which is a retention time of the $^{99m}$Tc-tricarbonyl precursor. As shown in FIG. 3b, a retention time of the $^{99m}$Tc-tricarbonyl cysteine complex was found to be 17 min. In both of two cases, radiolabeling efficiency was over 95%.

EXPERIMENTAL EXAMPLE 4

Assay for Radiochemical Purity and Labeling Efficiency of $^{99m}$Tc-DMSA

Figure 4A:
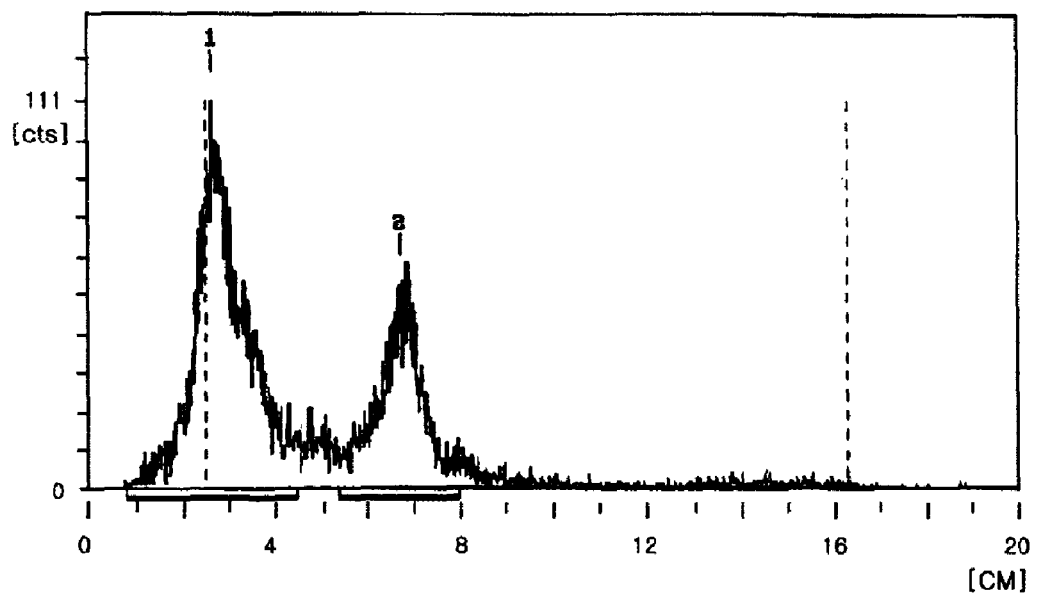
FIGS. 4a and 4b are results of TLC of $^{99m}$Tc-dimercaptosuccinic acid prepared in Example 4.
Figure 4B:
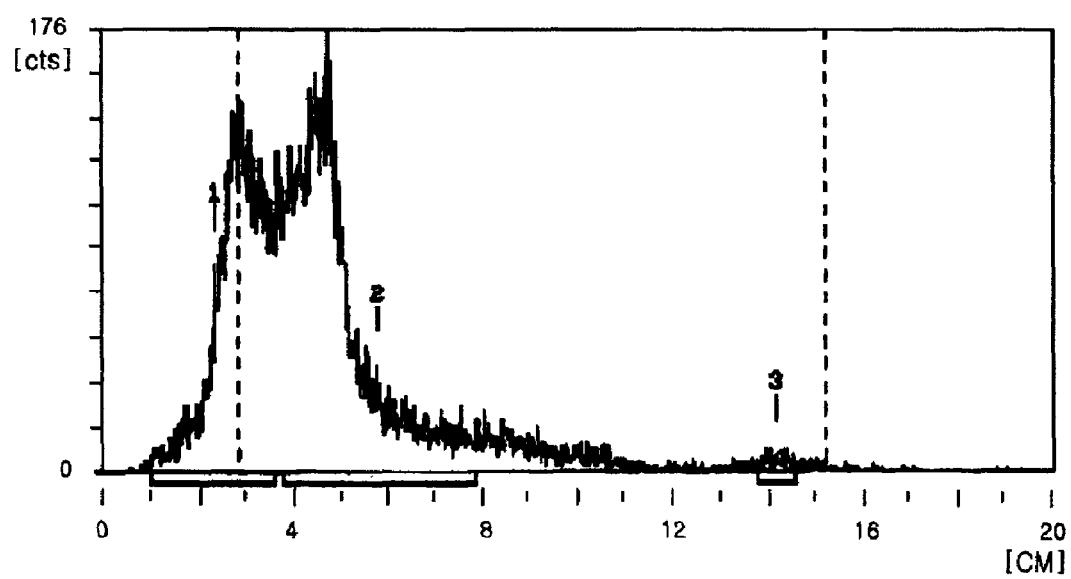

ITLC-SG for $^{99m}$Tc-dimercaptosuccinic acid ($^{99m}$Tc-DMSA), prepared in Example 4, was performed, using acetone or physiological saline as a development solvent, and the results are given in FIGS. 4a and 4b, respectively. As shown in FIG. 4a, no peak of $^{99m}$TcO$_4^-$ was observed at the solvent front, which is expected to migrate with the solvent front, indicating the formation of $^{99m}$Tc-DMSA having excellent labeling efficiency.

Figure 4C:
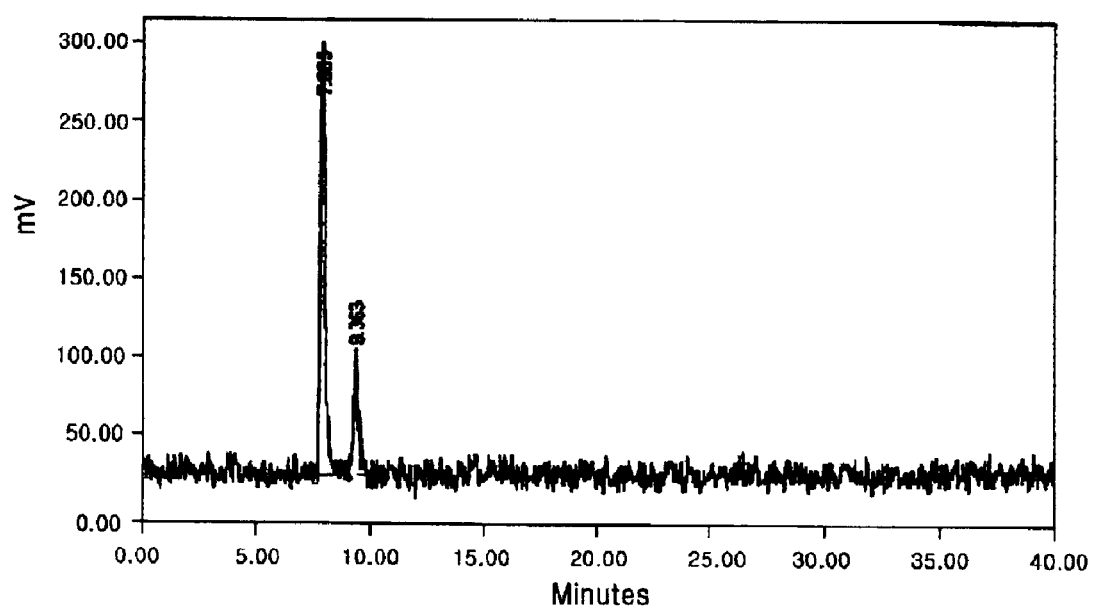
FIG. 4c is a result of HPLC of $^{99m}$Tc-dimercaptosuccinic acid prepared in Example 4.

Radiochemical purity of $^{99m}$Tc-DMSA was measured by performing, HPLC using a mixture of a phosphate-buffered triethylammonium solution/an acetonitrile as a mobile phase, while maintaining a flow rate of 1 ml/min, and the result is given in FIG. 4c. As shown in FIG. 4c, two peaks were observed at retention times of 7.9 min and 9.4 min, indicating the formation of $^{99m}$Tc-DMSA complexes having high radiochemical purity.

EXPERIMENTAL EXAMPLE 5

Assay for Labeling Efficiency of $^{99m}$Tc-MDP

Figure 5A:
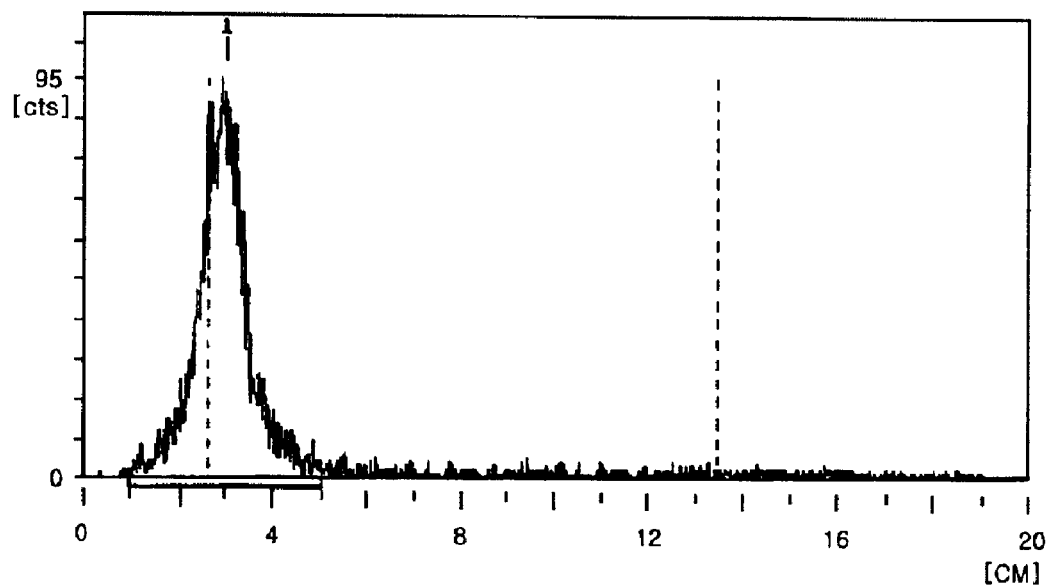
FIGS. 5a and 5b are results of TLC of $^{99m}$Tc-methylene diphosphate prepared in Example 5.
Figure 5B:
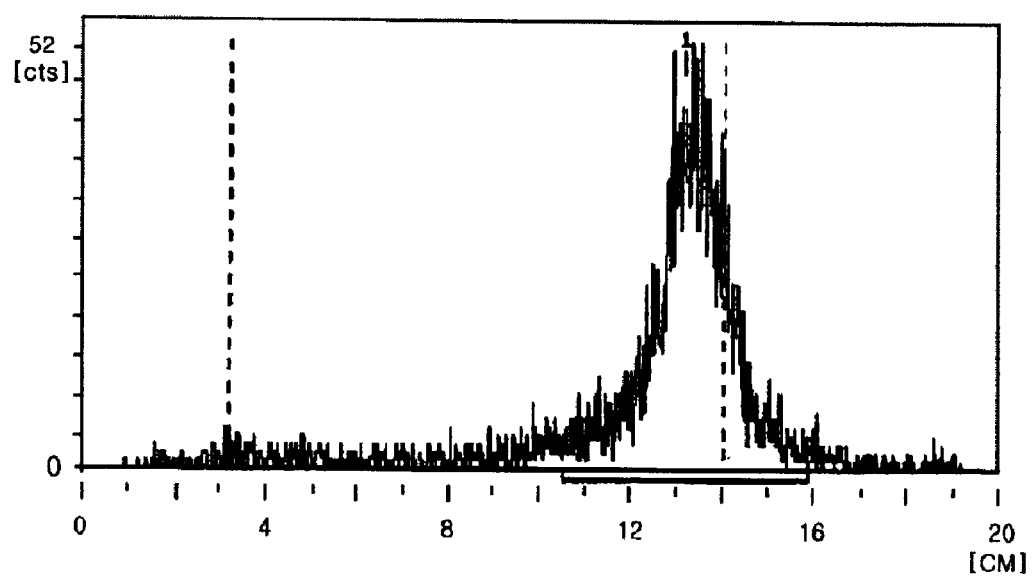

In order to investigate labeling efficiency of $^{99m}$Tc-methylene diphosphate ($^{99m}$Tc-MDP) prepared in Example 5, ITLC-SG was performed, using acetone or physiological saline as a development solvent, and the results are given in FIGS. 5a and 5b, respectively. As shown in FIG. 5a, there was no observation of a peak of $^{99m}$TcO$_4^-$ at the solvent front, which is expected to migrate with the solvent front. As shown in FIG. 5b, $^{99m}$TcO$_2$ was not observed at the origin. These results indicate that $^{99m}$Tc-MDP complexes having excellent labeling efficiency were formed.

EXPERIMENTAL EXAMPLE 6

Assay for Labeling Efficiency of $^{99m}$Tc-MAMA

Figure 6:
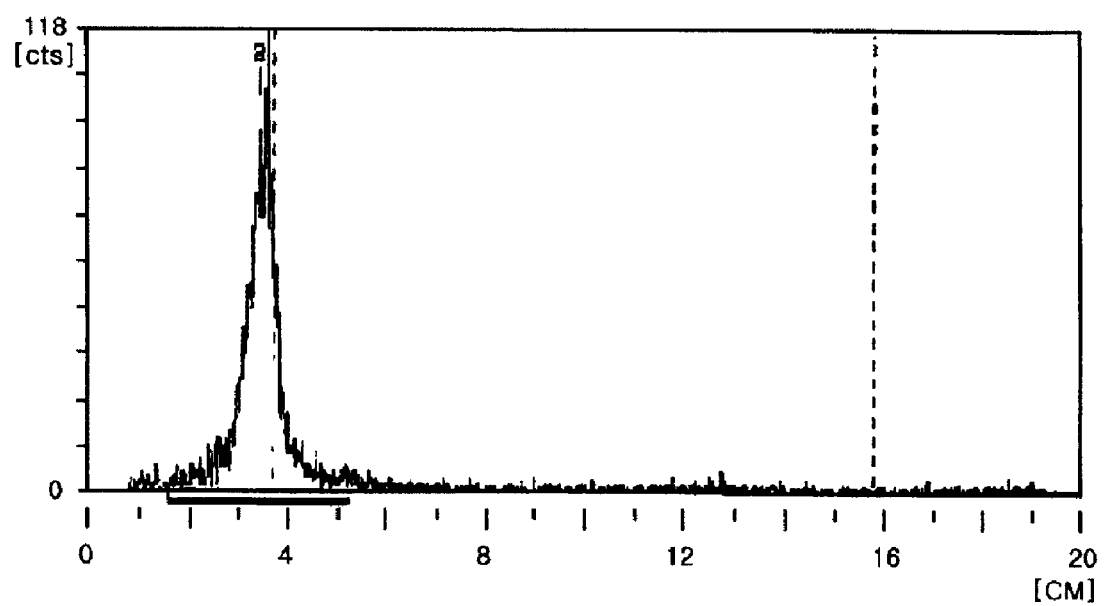
FIG. 6 is a result of TLC of $^{99m}$Tc-MAMA prepared in Example 6.

In order to investigate labeling efficiency of $^{99m}$Tc-MAMA prepared in Example 6, ITLC-SG was performed using acetone as a development solvent, and the result is given in FIG. 6. As shown in FIG. 6, no peak of $^{99m}$TcO$_4^-$ was observed at the solvent front, which is expected to migrate with the solvent front, indicating the formation of $^{99m}$Tc-MAMA complexes having excellent labeling efficiency.

EXPERIMENTAL EXAMPLE 7

Assay for Labeling Efficiency of $^{99m}$Tc-human Serum Albumin

Figure 7:
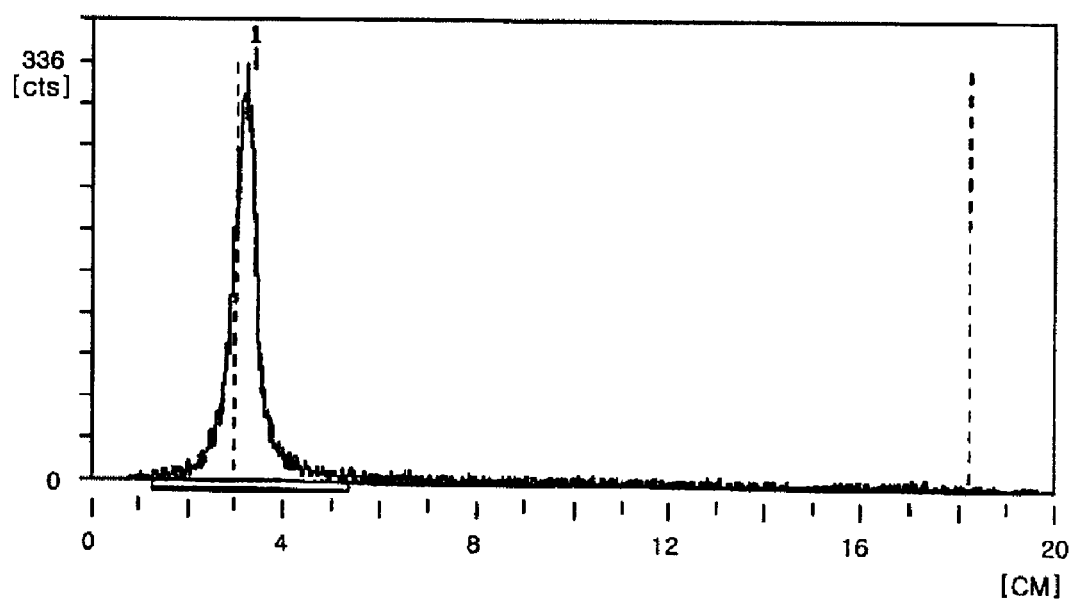
FIG. 7 is a result of TLC of $^{99m}$Tc-human serum albumin prepared in Example 7.

In order to investigate labeling efficiency of $^{99m}$Tc-human serum albumin prepared in Example 7, ITLC-SG was performed using acetone as a development solvent, and the result is given in FIG. 7. As shown in FIG. 7, no peak of $^{99m}TcO_4^-$ was observed at the solvent front, which is expected to migrate with the solvent front, indicating the formation of $^{99m}Tc$-human serum albumin complexes having excellent labeling efficiency.

EXPERIMENTAL EXAMPLE 8

Assay for Radiochemical Purity and Labeling Efficiency of $^{99m}TcN$-DADS

It is possible to be identified the formation of a novel technetium-labeled compound, by investigating position of a peak of Tc-99m pertechnetate using ITLC.

Figure 8A:
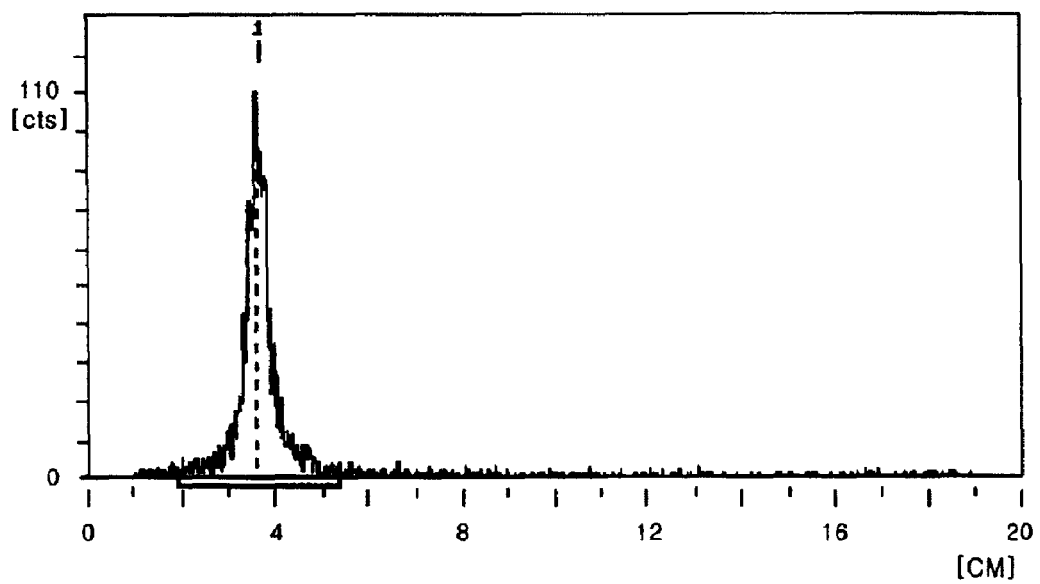
FIG. 8a is a result of TLC of $^{99m}$Tc-Nitrido prepared in Example 8.

For $^{99m}TcNCl_4^-$ prepared in Step 1 of Example 8, ITLC-SG was performed using acetone as a development solvent, and the result is given in FIG. 8a. As shown in FIG. 8a, there was no observation of a peak of $^{99m}TcO_4^-$ at the solvent front, which is expected to migrate with the solvent front, indicating the formation of $^{99m}TcNCl_4^-$ having excellent labeling efficiency.

Figure 8B:
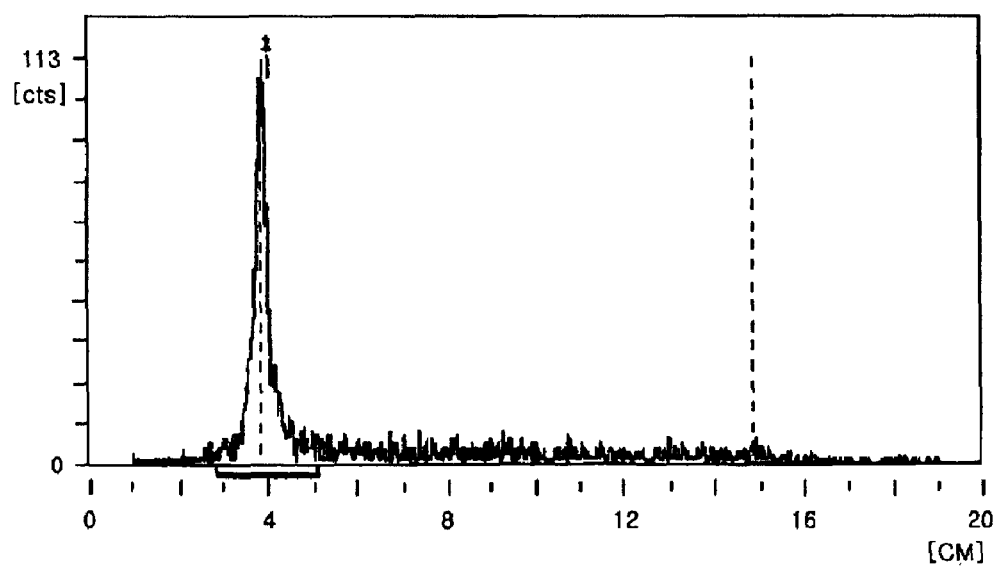
FIG. 8b is a result of TLC of $^{99m}$TcN-DADS prepared in Example 8.
Figure 8C:
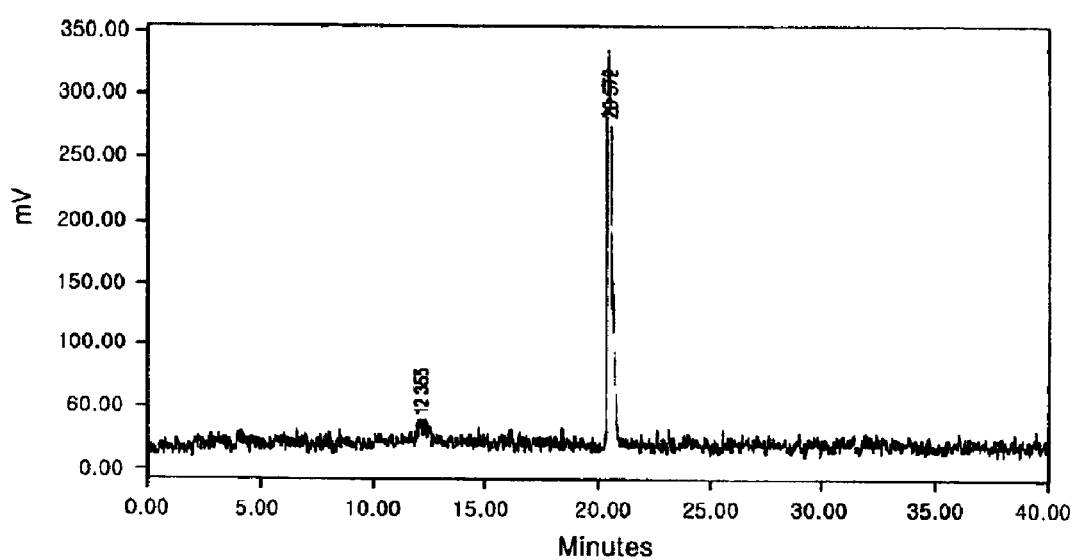
FIG. 8c is a result of HPLC of $^{99m}$TcN-DADS prepared in Example 8.

For $^{99m}TcN$-DADS prepared in Step 2 of Example 8 through reaction of $^{99m}TcNCl_4^-$ with DADS, ITLC-SG was performed and the results is given FIG. 8b, and HPLC was carried out using a mixture of water/acetonitrile as a mobile phase, while maintaining a flow rate of 1 ml/min, and the result is given in FIG. 8c.

As shown in FIG. 8c, one peak corresponding to the compound of interest was observed at a retention time of 20.6 min, indicating the formation of $^{99m}TcN$-DADS complexes having radiochemical purity of over 98%.

EXPERIMENTAL EXAMPLE 9

Figure 9A:
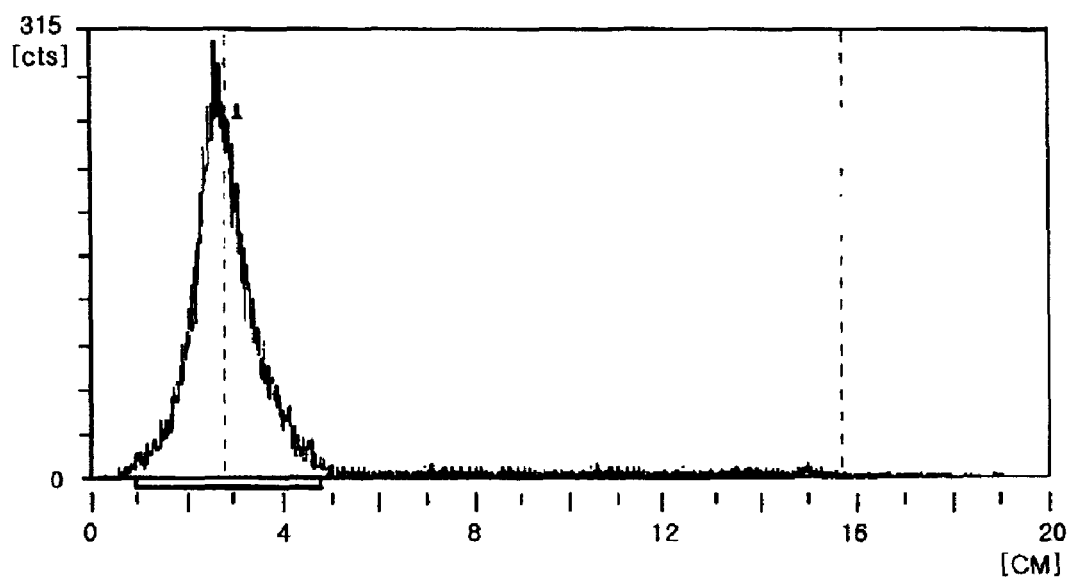
FIGS. 9a and 9b are results of TLC of $^{99m}$Tc-1-thio-β-D-glucose prepared in Example 9.
Figure 9B:
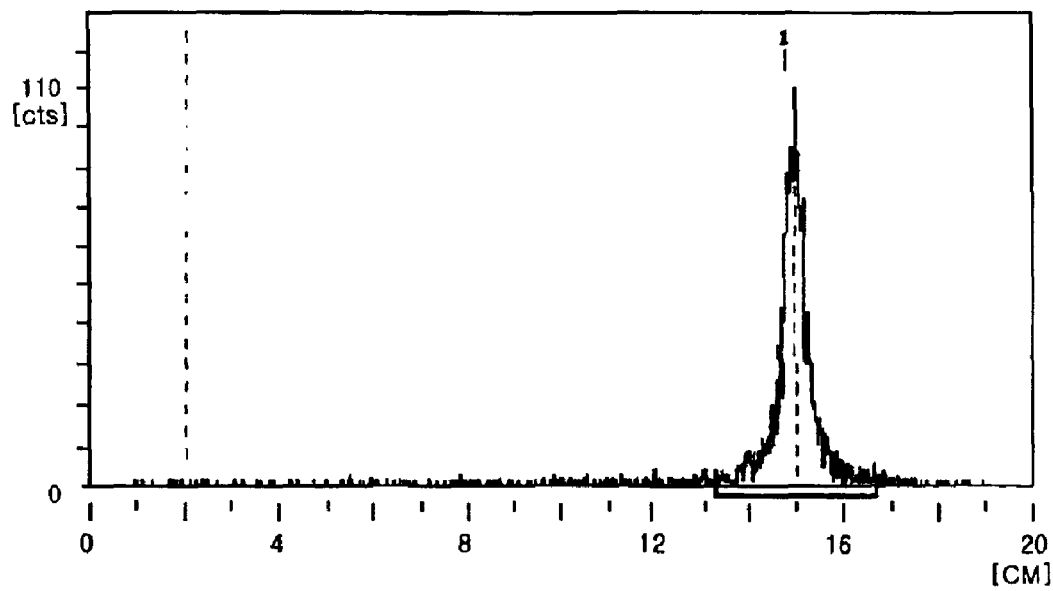

Assay for Radiochemical Purity and Labeling Efficiency of $^{99m}Tc$-1-thio-$\beta$-D-glucose ITLC-SG for $^{99m}Tc$-1-thio-$\beta$-D-glucose prepared in Example 9 was performed using acetone or physiological saline as a development solvent, and the results are given in FIGS. 9a and 9b, respectively. As shown in FIG. 9a, there was no observation of a peak of $^{99m}TcO_4^-$ at the solvent front, which is expected to migrate with the solvent front. As shown in FIG. 9b, $^{99m}TcO_2$ was not observed at origin. These results indicate that $^{99m}Tc$-1-thio-$\beta$-D-glucose complexes having excellent labeling efficiency were formed.

Figure 9C:
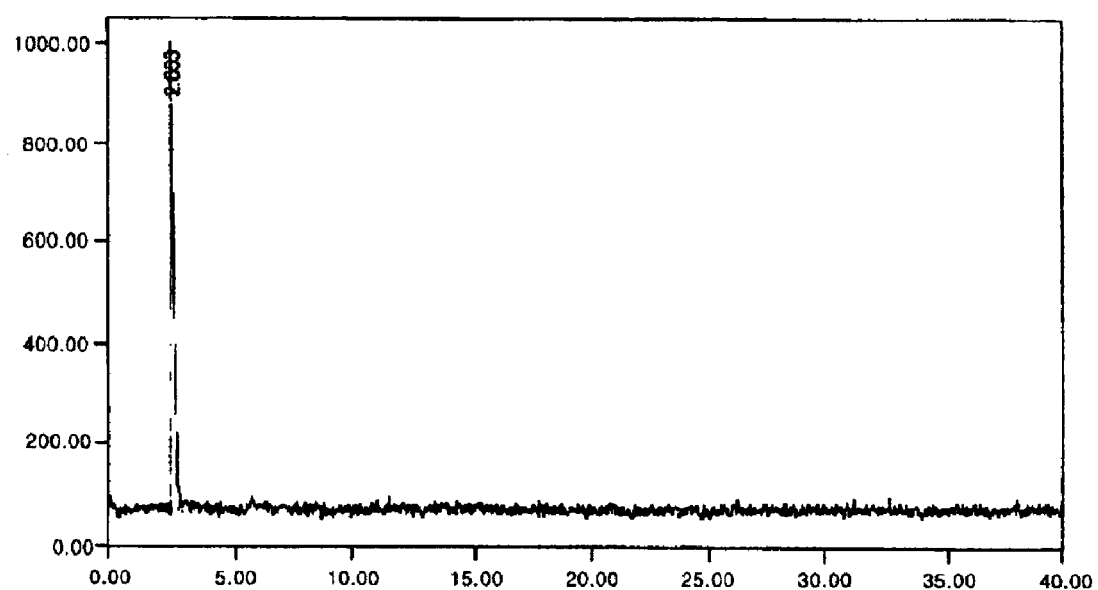
FIG. 9c is a result of HPLC of $^{99m}$Tc-1-thio-β-D-glucose prepared in Example 9.

Radiochemical purity of $^{99m}Tc$-1-thio-$\beta$-D-glucose was measured by performing HPLC using a mixture of water/acetonitrile as a mobile phase, while maintaining a flow rate of 1 ml/min, and the result is given in FIG. 9c. As shown in FIG. 9c, one peak corresponding to the compound of interest was observed at a retention time of 2.7 min, indicating the formation of $^{99m}Tc$-1-thio-$\beta$-D-glucose complexes having radiochemical purity of over 99%.

EXPERIMENTAL EXAMPLE 10

Assay for Labeling Efficiency of $^{99m}Tc$-glycylglycylglycine

Figure 10:
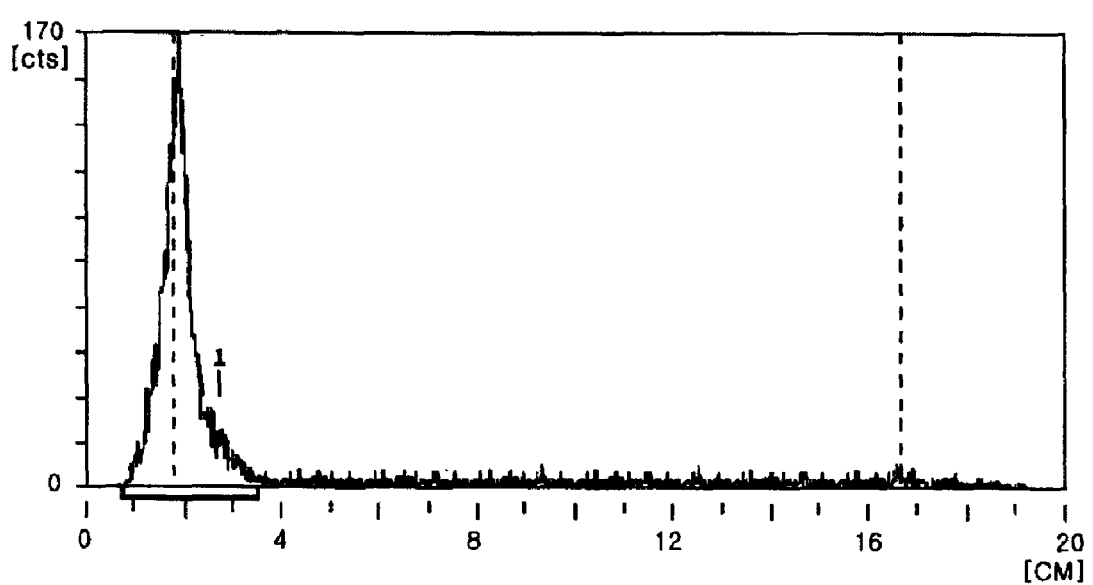
FIG. 10 is a result of TLC of $^{99m}$Tc-glycylglycylglycine prepared in Example 10.

In order to investigate labeling efficiency of $^{99m}Tc$-glycylglycylglycine prepared in Example 10, ITLC-SG was performed using acetone as a development solvent, and the result is given in FIG. 10. As shown in FIG. 10, there was no observation of a peak of $^{99m}TcO_4^-$ at the solvent front, which is expected to migrate with the solvent front, indicating the formation of $^{99m}Tc$-glycylglycylglycine complexes having excellent labeling efficiency.

EXPERIMENTAL EXAMPLE 11

Assay for Labeling Efficiency of $^{99m}Tc$-human IgG

Figure 11:
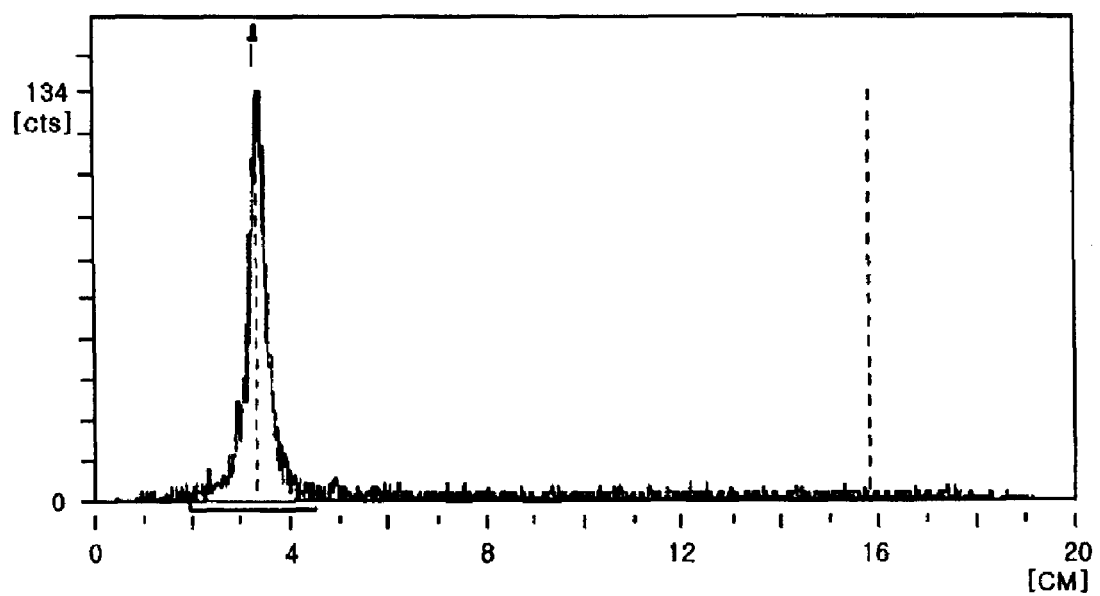
FIG. 11 is a result of TLC of $^{99m}$Tc-human IgG prepared in Example 11.

In order to investigate labeling efficiency of $^{99m}Tc$-human IgG prepared in Example 11, ITLC-SG was performed using acetone as a development solvent, and the result is given in FIG. 11. As shown in FIG. 11, there was no observation of a peak of $^{99m}TcO_4^-$ at the solvent front, which is expected to migrate with the solvent front, indicating the formation of $^{99m}Tc$-human IgG complexes having excellent labeling efficiency.

EXPERIMENTAL EXAMPLE 12

Assay for Labeling Efficiency and Radiochemical Purity of $^{188}Re$-DADS

Figure 12A:
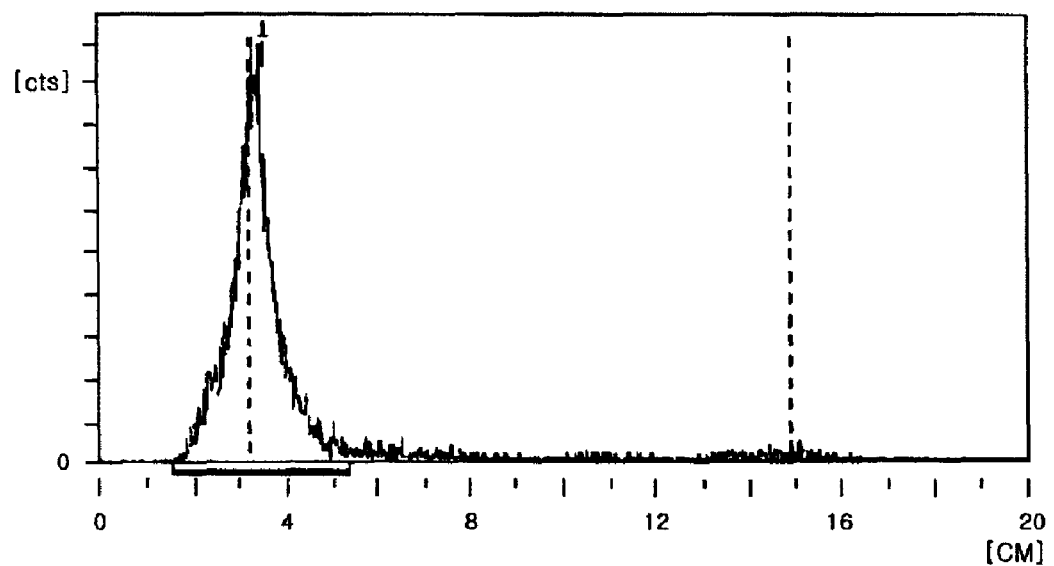
FIG. 12a is a result of TLC of $^{188}$Re-diamine disulfide prepared in Example 12.

In order to investigate labeling efficiency of $^{188}Re$-DADS prepared in Example 12, ITLC-SG was performed using acetone as a development solvent, and the result is given in FIG. 12a. As shown in FIG. 12a, there was no observation of a peak of $^{99m}TcO_4^-$ at the solvent front, which is expected to migrate with the solvent front, indicating the formation of $^{188}Re$-DADS having excellent labeling efficiency.

Figure 12B:
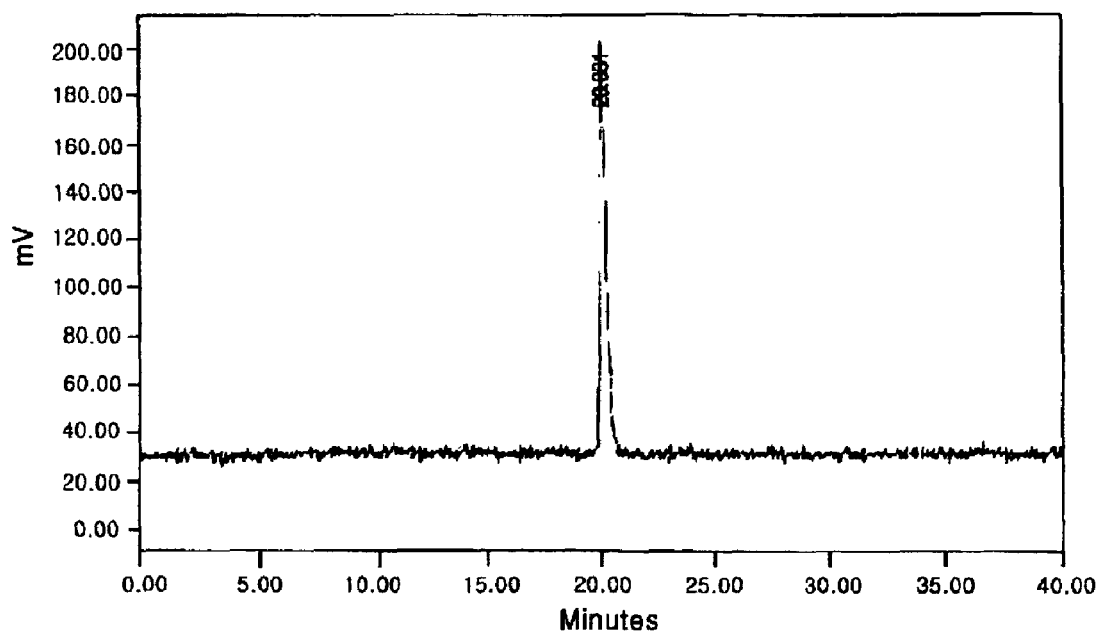
FIG. 12b is a result of HPLC of $^{188}$Re-diamine disulfide prepared in Example 12.

To evaluate radiochemical purity of $^{188}Re$-DADS, HPLC was performed using a mixture of water/acetonitrile compound as a mobile phase, while maintaining a flow rate of 1 ml/min, and the result is given in FIG. 12b. As shown in FIG. 12b, one peak was observed at a retention time of 20 min, indicating the formation of $^{188}Re$-DADS complexes having radiochemical purity of over 98%.

EXPERIMENTAL EXAMPLE 13

Assay for Labeling Efficiency of $^{188}Re$-Nitrido

Figure 13:
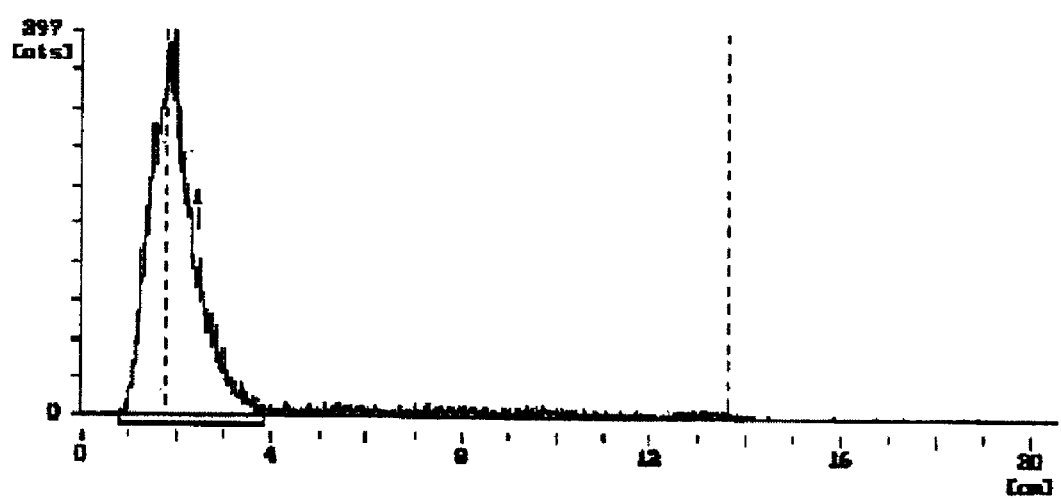
FIG. 13 is a result of TLC of $^{188}$Re-Nitrido prepared in Example 13.

In case of $^{188}Re$-Nitrido, ITLC-SG was performed using acetone as a development solvent, and the result is given in FIG. 13. As shown in FIG. 13, there was no observation of a peak of $^{99m}TcO_4^-$ at the solvent front, which is expected to migrate with the solvent front, indicating the formation of a $^{188}Re$-Nitrido precursor having excellent labeling efficiency.

INDUSTRIAL APPLICABILITY

As described hereinbefore, according to the present invention, employing the borohydride exchange resin (BER) as a novel reducing agent, technetium or rhenium complexes having high radiochemical purity as well as high labeling efficiency can be prepared by reacting pertechnetate or perrhenate with a ligand. The BER is advantageous in terms of being stable in most pH ranges including extreme acidic and alkaline pH conditions and applicable to biological materials, as well as being easily removable through filtration when being administrated, thus providing the potential to economically and effectively produce technetium or rhenium radiopharmarceuticals by replacing the conventional reducing agent requiring very stringent condition for preparation thereof.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method of preparing technetium or rhenium complexes for radiopharmaceuticals, comprising reacting pertechnetate or perrhenate with a ligand in the presence of a reducing agent, wherein the reducing agent is a borohydride exchange resin.

2. The method according to claim 1, wherein the ligand comprises a functional group selected from the group consisting amine, carboxy group, thiolate, nitrido, isocyanate, alcohol, ester, halogen atom, alkoxy group, sulfonic acid, nitro group, amide group, nitrile group, isonitrile group, and mixtures thereof.

3. The method according to claim 1, wherein the ligand is selected from the group consisting of nitrido, glucoheptonate, L-cysteine, L-cysteine.HCl.H$_2$O, diamine disulfide, dimercaptosuccinic acid, thio-β-D-glucose, methylene diphosphate, diethylenetriamine pentaacetic acid, N-[2-((triphenyl methyl)thio)ethyl) acethyl]-S-(triphenyl methyl)-2-aminoethanthiol, and mixtures thereof.

4. The method according to claim 1, wherein the ligand is a physiologically active material selected from at least one of human serum albumin, peptide and human immunoglobulin.

5. The method according to claim 1, wherein the ligand and pertechnetate or perrhenate are added together to the borohydride exchange resin.

6. The method according to claim 1, wherein the pertechnetate or perrhenate is added to a mixture of a borohydride exchange resin and a ligand.

7. A kit for radiolabelling with technetium or rhenium, comprising a ligand and a borohydride exchange resin.

8. The kit according to claim 7, being lyophilized or dried at room temperature, stored in a sterile vessel, and maintained under inert gas atmosphere.

9. The kit according to claim 8, wherein the inert gas atmosphere comprises a nitrogen atmosphere.

* * * * *